United States Patent [19]

Warriner

[11] Plant 5,000

[45] Mar. 22, 1983

[54] ROSE PLANT—74-2179-18

[75] Inventor: William A. Warriner, Tustin, Calif.

[73] Assignee: Jackson & Perkins Company, Medford, Oreg.

[21] Appl. No.: 299,959

[22] Filed: Sep. 8, 1981

[51] Int. Cl.[3] ..... A01H 5/00

[52] U.S. Cl. ..... Plt./20

[58] Field of Search ..... Plt./11, 20

*Primary Examiner*—Robert E. Bagwill

*Attorney, Agent, or Firm*—Klarquist, Sparkman, Campbell, Leigh, Whinston & Dellett

[57] ABSTRACT

A hybrid tea rose variety having an upright growth habit, large pink blooms darkening to red upon sunlight exposure, and little fragrance.

1 Drawing Figure

This present invention relates to a new and distinct variety of rose plant of the hybrid tea class which was originated by me by crossing the variety Sunfire, U.S. Plant Pat. No. 3,510, with the variety Spellbinder, U.S. Plant Pat. No. 3,571.

The primary objective of this breeding was to produce a new rose variety combining the abundance of flowering of Sunfire with the photosensitive pigment characteristics of Spellbinder. This objective was substantially achieved along with other desirable improvements as evidenced by the following unique combination of characteristics which are outstanding in the new variety and which distinguish it from its parents as well as from all other varieties of which I am aware:

1. An upright hybrid tea habit of growth.
2. Large blooms of a pink color that darkens to a red upon exposure to sunlight.
3. Little or no fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Sunfire, U.S. Plant Pat. No. 3,510.

*Pollen parent.*—Spellbinder, U.S. Plant Pat. No. 3,571.

Classification:

*Botanical.*—Rosa hybrid.

*Commercial.*—Hybrid tea.

FLOWER

Observations made from specimens grown at Irvine, Calif. in August.

Blooming habit: Continuous.

Bud:

*Size.*—1¼" when petals start to unfurl.

*Form.*—Blunt top, ovoid.

*Color.*—When sepals first divide, Red 47A after exposure to sunlight, Pink (RHS Red 47D) when first exposed; when half blown, upper side of petals Red 47D darkening to Red 47A; lower side of petals varies depending on exposure from Red 47D, mostly near base, to Red 47A, mostly near tips.

*Sepals.*—Color: Outer surface mostly Green 138B also having numerous stipitate glands; three appendaged sepals lightly appendaged; two unappendaged sepals hairy edged.

*Receptacle.*—Color: Green 138B with brown shading. Shape: Funnel, upper end sometimes constricted. Size: Large, long. Surface: Glandular.

*Peduncle.*—Length: Short. Surface: Glandular. Color: Bronzy. Strength: Stiff, erect.

*Opening.*—Petals fold outward gradually.

Bloom:

*Size.*—Large. Average open size 4".

*Borne.*—Singly.

*Stems.*—Long.

*Form.*—When first open, high center. Permanence: Retains its form; outer edge slightly curled.

*Petalage.*—Number of petals under normal conditions 35–40.

*Color.*—Center of flower: Upper side of petals upon first opening Pink (Red 47D) aging when exposed to daylight to Red 47A. Reverse side of petals mostly Red 47D aging in some parts of the petal to 47A. Base of petals very light yellow. General tonality from a distance blend of Red 47A lightened in shaded areas of the petals to 47A.

*Variegations.*—Occasional green streaks of vegetative nature on outer petals.

*Discoloration.*—Third day: More area of Red 47A, sometimes a little darker.

*Fragrance.*—None.

Petals:

*Texture.*—Normal thickness.

*Shape.*—Nearly round.

*Form.*—Tips slightly recurved.

*Arrangement.*—Imbricated. Petaloids in center, few.

*Persistence.*—Drop off cleanly.

*Lastingness.*—On the plant, long. As cut flowers, long.

Reproductive parts:

*Anthers.*—Medium. Color: Yellow. Arrangement: Regular around styles.
*Filaments.*—Color: Reddish.
*Pollen.*—Lemon yellow.
*Styles.*—Color: Pink.
*Stigmas.*—Color: Yellow.

PLANT

Form: Bush.
Growth: Very vigorous, upright.
Foliage:
*Number of leaflets on normal mid-stem leaves*—Usually 5.
*Size.*—Large.
*Quantity.*—Normal.
*Color.*—New foliage: Brown to Red-Purple 59A. Old foliage: Green 133A.
Leaflets:
*Shape.*—Oval.
*Texture.*—Upper side, leathery.
*Edge.*—Serrated.
*Serration.*—Single, small.
*Petiole.*—Rachis: Color, reddish. Underside: Prickles.

*Stipules.*—Long.
*Disease resistance.*—Mildly susceptible to mildew under normal growing conditions at Irvine, Calif.
Wood:
*New wood.*—Color: Bronzy brown. Bark: Smooth.
*Old wood.*—Color: Green to brown. Bark: Smooth.
Prickles:
*Quantity.*—On main stalks from base, ordinary. On laterals from stalk, ordinary.
*Form.*—Long base, hooked downward.
*Color when young.*—Brown.
*Position.*—Irregular.
Small prickles:
*Quantity.*—On main stalks, none. On laterals, none.

I claim:

1. A new and distinct variety of rose plant of the hybrid tea class, substantially as herein shown and described, characterized particularly as to novelty by the unique combination of its hybrid tea plant habit with non-fragrant blooms with photosensitive pigment changing from pink to red upon exposure to sunlight.

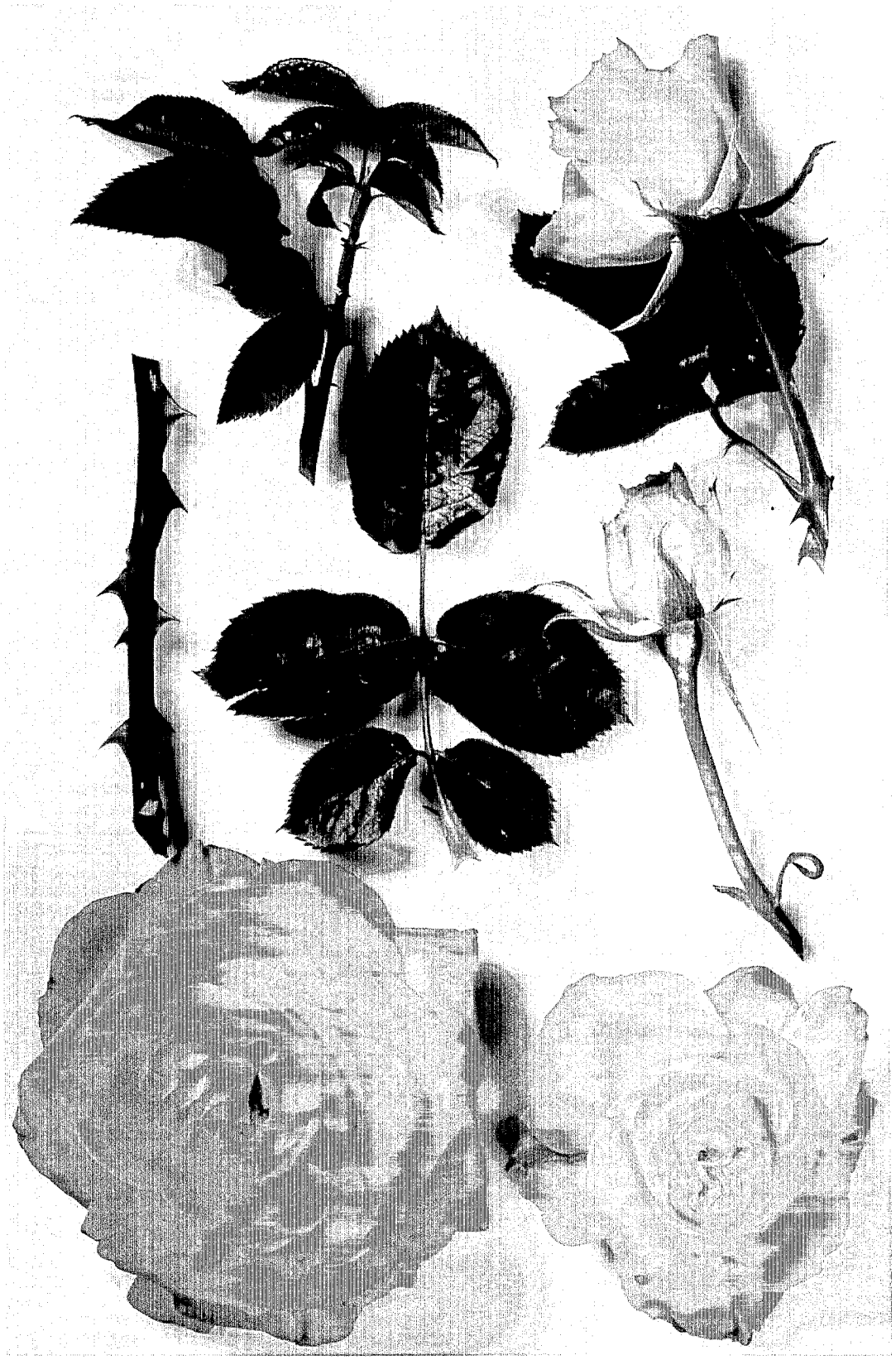

* * * * *